(12) United States Patent
Lee et al.

(10) Patent No.: US 9,655,891 B1
(45) Date of Patent: May 23, 2017

(54) USE OF ISOQUINOLINE DERIVATIVES FOR DIABETIC WOUND HEALING

(71) Applicant: ZIH YUAN TANG Biotechnology Co., Ltd, Taipei (TW)

(72) Inventors: Shoei-Sheng Lee, Taipei (TW); Ming-Jai Su, Taipei (TW); Chi-Huan Yeh, Miaoli County (TW); Chao-Min Hsu, New Taipei (TW)

(73) Assignee: ZIH YUAN TANG BIOTECHNOLOGY CO., LTD, Taipei (TW)

( * ) Notice: Subject to any disclaimer, the term of this patent is extended or adjusted under 35 U.S.C. 154(b) by 0 days.

(21) Appl. No.: 15/166,964

(22) Filed: May 27, 2016

Related U.S. Application Data

(60) Provisional application No. 62/291,923, filed on Feb. 5, 2016.

(51) Int. Cl.
*A61K 31/472* (2006.01)
*C07D 217/00* (2006.01)

(52) U.S. Cl.
CPC .......... *A61K 31/472* (2013.01); *C07D 217/00* (2013.01)

(58) Field of Classification Search
CPC ........................... A61K 31/472; C07D 217/00
See application file for complete search history.

(56) References Cited

PUBLICATIONS

Byun et al (Investigative Ophthalmolog & Visual Science, Mar. 2015, vol. 56, No. 3, pp. 1948-1955).*
Praman et al (Journal of Ethnopharmacology, 2012, 140, 166-178).*
Kurnik et al (Folia Medica Cracoviensia (2012, 52(3-4), pp. 5-20).*
Guo et al (J.Dent.Res., 2010, 89(3). 219-229).*

* cited by examiner

*Primary Examiner* — Sudhakar Katakam
(74) *Attorney, Agent, or Firm* — Birch, Stewart, Kolasch & Birch, LLP

(57) ABSTRACT

The present invention is related to a method for diabetic wound healing comprising administering to a subject in need thereof a pharmaceutical composition comprising a pharmaceutically acceptable carrier and a therapeutically effective amount of a compound having the general Formula I, preferably salsolinol.

3 Claims, 3 Drawing Sheets

USE OF ISOQUINOLINE DERIVATIVES FOR DIABETIC WOUND HEALING

RELATED APPLICATIONS

This application claims the benefit of U.S. provisional application No. 62/291,923, filed Feb. 5, 2016, the entire content of which is incorporated herein by reference.

FIELD OF THE INVENTION

The present invention provides a method for diabetic wound healing. In particular, the present invention provides a new use of isoquinoline derivatives for diabetic wound healing.

BACKGROUND OF THE INVENTION

Isoquinoline derivatives are a group of nitrogen-containing organic compounds existing in plants and animals in nature. Most of them have a complex ring structure with their nitrogen atom incorporated in the ring. Such isoquinoline derivatives, including salsolinol and reticuline, possess significant biological activities. Salsolinol is known to be used mainly for regulation of blood pressure, while reticuline is used mainly as an active ingredient for treating malaria, and also as a component in pain relievers.

It is disclosed in U.S. patent application Ser. No. 14/492,547 that isoquinoline derivatives, including salsolinol and reticuline, can activate AMP-dependent protein kinase (AMPK) and use in treatment of AMPK-dependent diseases. However, no prior art references report the effect of isoquinoline derivatives in treatment of diabetic wound healing.

Diabetes mellitus can be virtually harmless if controlled, but the state of abnormally high blood glucose levels associated with the condition can lead to some serious complications. If left uncontrolled for a long time, or if diabetic patients fail to adapt their lifestyles in order to manage the disease, they will have more difficulty preventing complications from occurring. A serious complication that diabetics may encounter is diabetic wounds.

The main concern with diabetic wounds is poor or delayed healing. Healing problems are caused by the peripheral arterial diseases and peripheral neuropathy that can occur with diabetes, wherein the small blood vessels in different parts of the body, especially in the extremities (hands and feet), grow narrower and reduce the blood circulation to those areas. A lack of circulation in the extremities can result in a reduced supply of oxygen and nutrients to the body tissue and nerves, which is necessary for healing. Over time, nerves in these areas may become damaged, decreasing the sensation of pain, temperature and touch, making patients vulnerable to injury.

There is a long felt need in the art for methods to treat diabetic wounds. The present invention satisfies this need.

BRIEF SUMMARY OF THE INVENTION

It is unexpectedly found in the present invention that certain isoquinoline derivatives, such as salsolinol, are effective in diabetic wound healing.

In one aspect, the present invention provides a method for diabetic wound healing comprising administering to a subject in need thereof a pharmaceutical composition comprising a pharmaceutically acceptable carrier and a therapeutically effective amount of a compound having the general Formula I:

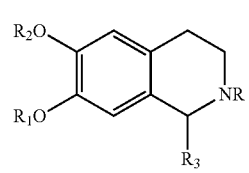

Formula I wherein R, $R_1$ and $R_2$ are each independently H, alkyl or acyl ($R_aCO$) group; $R_3$ is H, alkyl or substituted benzyl group; wherein $R_a$ is H or alkyl group.

In one embodiment of the present invention, said substituted benzyl group has the following formula II:

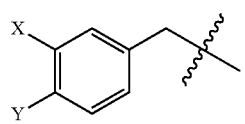

Formula II wherein X and Y are each independently H, OH, methoxy (OMe) or acyloxy ($R_bCO$—O—) group; wherein $R_b$ is H or alkyl group.

In one example of the present invention, said compound having Formula I is salsolinol.

In another aspect, the present invention provides a use of a compound having the general Formula I of the present invention in manufacture of a medicament for diabetic wound healing.

Those and other aspects of the present invention may be further clarified by the following descriptions and drawings of preferred embodiments. Although there may be changes or modifications therein, they would not betray the spirit and scope of the novel ideas disclosed in the present invention.

BRIEF DESCRIPTION OF THE DRAWINGS

The drawings presenting the preferred embodiments of the present invention are aimed at explaining the present invention. It should be understood that the present invention is not limited to the preferred embodiments shown. The data in the figures and examples are shown as mean±standard deviation (SD), determined by the paired t-test. Significant differences are shown as follows: *: $P<0.05$; **: $P<0.01$.

DETAILED DESCRIPTION OF THE INVENTION

Figure 1:
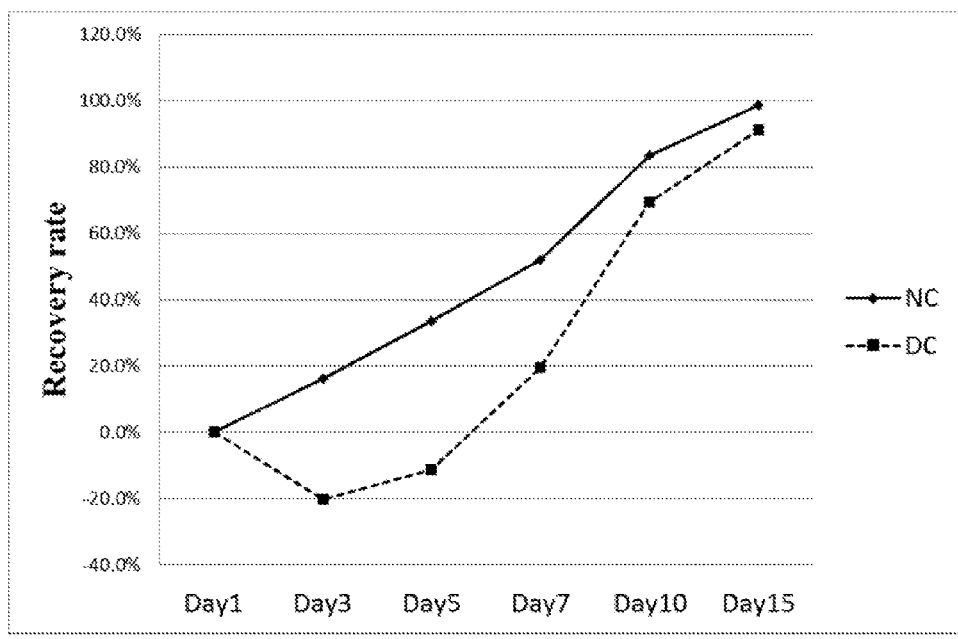
FIG. 1 shows the recovery rates of the wounds of normal rats without treatment (NC) and STZ induced diabetic rats without treatment (DC) for 15 days.

Unless defined otherwise, all technical and scientific terms used herein have the same meanings as commonly understood by one of skill in the art to which this invention belongs.

Unless clearly specified herein, meanings of the articles "a," "an," and "said" all include the plural form of "more than one." Therefore, for example, when the term "a component" is used, it includes multiple said components and equivalents known to those of common knowledge in said field.

As used herein, the term "substituted" or "substitution" refers to where a functional group in a chemical compound is replaced by another group.

As used herein, the term "subject" refers to a human or a mammal, such as a patient, a companion animal (e.g., dog, cat, and the like), a farm animal (e.g., cow, sheep, pig, horse, and the like) or a laboratory animal (e.g., rat, mouse, rabbit, and the like).

The term "alkyl group" used herein refers to linear or branched monovalent hydrocarbons containing 1-20 carbon atoms, such as alkyl groups with 1-10 carbons, preferably alkyl groups with 1-6 carbons, more preferably alkyl groups with 1-3 carbons. Examples of alkyl groups include, but not limited to, methyl, ethyl, n-propyl, isopropyl, n-butyl, isobutyl, and t-butyl.

Accordingly, the invention, in one aspect, provides a method for diabetic wound healing. The method comprises administering to a subject in need thereof a pharmaceutical composition comprising a pharmaceutically acceptable carrier and a therapeutically effective amount of a compound having the general Formula I:

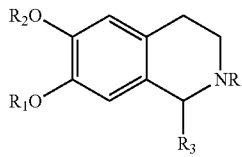

Formula I wherein R, $R_1$ and $R_2$ are each independently H, alkyl or acyl ($R_aCO$) group; $R_3$ is H, alkyl or substituted benzyl group; wherein $R_a$ is H or alkyl group.

In a particular example of the present invention, said substituted benzyl group has the following Formula II:

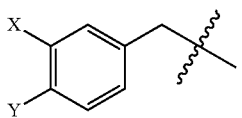

Formula II wherein X and Y are each independently H, OH, methoxy (OMe) or acyloxy ($R_bCO—O—$) group; wherein $R_b$ is H or alkyl group.

An embodiment of the active compound of the present invention is the compound having the general Formula I, wherein R=$R_1$=$R_2$=H and $R_3$=Me (methyl), which compound is salsolinol having the following formula:

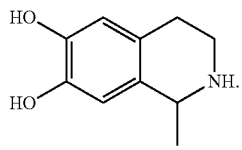

As shown in the examples of the present invention, the compound having Formula I of the present invention, such as salsolinol, has an effect of treating diabetic wounds.

According to the present invention, said compound having Formula I can be formulated into any forms of medications that are well known or commonly used in the pharmaceutical field, and can be prepared into a composition, according to any techniques well known in the pharmaceutical field, comprising a therapeutically effective amount of said compound in combination with a commonly used carrier or a pharmaceutically acceptable carrier.

The term "carrier" or "pharmaceutically acceptable carrier" used herein includes, but not limited to, pharmaceutically acceptable excipients, fillers, diluents, or the like, including those well known to one of ordinary skills in the pharmaceutical field.

The present invention is explained in the above description of the invention and the following examples, which should not be used to restrict the scope of the present invention.

Example

1. Preparation of the Compound Having Formula I of the Present Invention

Dopamine (1.6 g), 10 mL methanol, 1 mL 1N hydrochloric acid, and 2 mL 99% acetaldehyde were added sequentially into a 50 mL round-bottom flask and stirred for 6 hours under room temperature. The concentrate obtained by reduced-pressure concentration was loaded into a Lobar RP-18 column (size B, Merck), eluted by a 0.05% formic acid aqueous solution, to give $^1$HNMR essential pure salsolinol (1.0 g).

Using ESI-TOF mass spectrometry and NMR spectroscopy analysis, the characterization data of salsolinol are as follows:

$^1$H NMR (CD$_3$OD, 400 MHz) δ 6.63 (1H, s), 6.57 (1H, s), 4.30 (1H, q, J=6.8 Hz, H-1), 3.40 (1H, dt, J=12.6, 5.6 Hz, H$_a$-3), 3.20 (1H, ddd, J=12.6, 8.2, 5.6 Hz, H$_b$-3), 2.92 (1H, ddd, J=16.8, 8.2, 5.8 Hz, H$_a$-4), 2.80 (1H, dt, J=16.8, 5.6 Hz, H$_b$-4), 1.55 (3H, d, J=6.8 Hz, Me-1); ESIMS: m/z 180 ([M+H]$^+$).

2. Evaluation of the Effect of Salsolinol in Treatment of Diabetic Wounds

Salsolinol ointments at 0.01 mg/g, 0.03 mg/g, 0.1 mg/g, and 0.3 mg/g were prepared respectively by dissolving 0.5 mg, 1.5 mg, 5 mg, and 15 mg of salsoinol in 2.5 mL of glycerol (Sigma Inc., MO, USA) plus 1.0 mL of Creagel emulsifier (First Chemical, TPE, Taiwan) and 45.5 mL of distilled water. Vehicle was composed of glycerol (2.5 mL), Creagel emulsifier (1.0 mL), and distilled water (45.5 mL).

Swivazin®-HN cream was used as positive control for treating the wounds of STZ induced diabetic rats, which contained asiaticoside (4 mg/g), isolated from *Centella asiatica*. It was reported by Shukla et al., that asiaticoside had the effects on ameliorating poor diabetic wound healing. [Shukla et al. In vitro and in vivo wound healing activity of asiaticoside isolated from *Centella asiatica*. Ethnopharmacology 65 (1999): 1-11].

Adult male Wistar rats were used at four weeks of age, purchased from BioLASCO Taiwan, and were acclimatized in a room with 12-12 h light (7:00 A.M. to 7:00 P.M.)-dark (7:00 P.M. to 7:00 A.M.) cycle, a temperature of 23±1° C., and a humidity of 65±5%.

Each rat had free access to both water and standard rodent soft chow ad libitum. STZ was injected intraperitoneally at a dose of 65 mg/Kg body weight. A week later, the rats that had a blood glucose level higher than 250 mg/dL were considered as STZ induced diabetic rats and used for experiments.

All experimental procedures were approved by and performed in compliance with the guidelines of the Institutional Animal Care and Use Committee (IACUC). All surgeries were conducted while animals were under continuous anesthesia with 4% isoflurane.

The dorsal skin was shaved and then disinfected with 10% povidone-iodine before an excisional full-thickness square-shaped skin wound (1.5×1.5 cm) was induced using a sterile wound maker. Animal was then housed alone in its cage to avoid any further wound damage.

Rats were randomly divided into eight groups (n=6, each group) as follows: normal rats (NC) for comparison, STZ induced diabetic rats without treatment (DC), STZ induced diabetic rats treated with the vehicle only (DV), STZ induced diabetic rats treated with Swivazin®-HN cream as positive control (DP, wherein the Swivazin®-HN cream contains 4 mg/g asiaticoside from *Centella asiatica*), and STZ induced diabetic rats treated with salsolinol (D+Salsolinol) at different concentrations of 0.01 mg/g, 0.03 mg/g, 0.1 mg/g, and 0.3 mg/g respectively. The groups were administered at the same amount once daily and the wounds were photopictured on Day 1, Day 3, Day 5, Day 7, Day 10, and Day 15 and the sizes of the wounds were analyzed using Visual Basic 6.0. Wound closure at experimental time points was calculated as percentage of initial wound area, called as "recovery rate."

In this example, the rats were injected with STZ intraperitoneally to obtain STZ induced diabetic rats, which had increased blood glucose levels (>250 mg/dL). The wounds of normal rats without treatment (NC) and diabetic rats without treatment (DC) were compared. As shown in FIG. 1, the wounds of NC recovered quickly in the beginning and the recovery rate over 98% at Day 15, while the wound healing of DC showed slower in terms of lower recovery rates as compared with normal rats (NC), and the wounds of DC were found to be even worse at Day 1-3. It was indicated that the wound healing of the STZ induced diabetes rats was poor and delayed.

Figure 2:
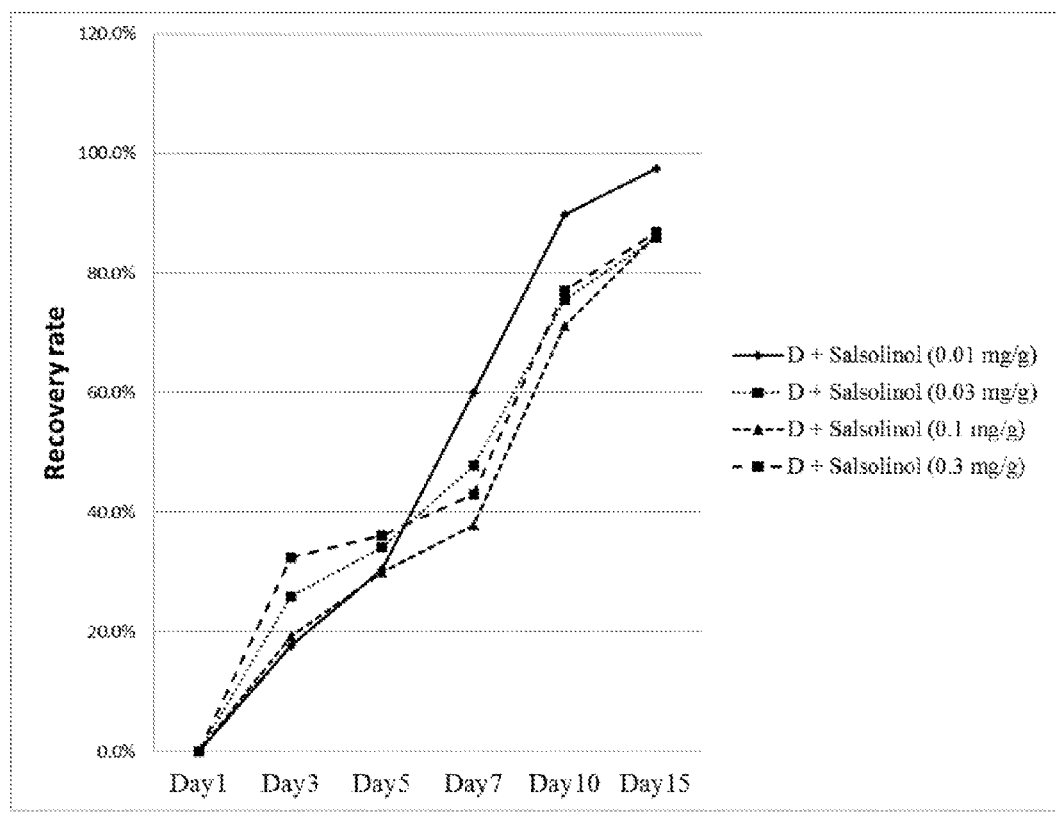
FIG. 2 shows the recovery rates of the wounds of STZ induced diabetic rats treated with salsolinol at different concentrations (0.01 mg/g, 0.03 mg/g, 0.1 mg/g, and 0.3 mg/g) for 15 days.

The STZ induced diabetic rats were divided into four groups and treated with salsolinol at the concentrations of 0.01 mg/g, 0.03 mg/g, 0.1 mg/g and 0.3 mg/g, respectively. As shown in FIG. 2, for the groups treated with salsolinol at all the concentrations, salsolinol could enhance the wound closure and healing. In particular, the group treated with salsolinol at the concentration of 0.01 mg/g showed relatively improved recovery rate at Day 7-15 (over 97% at Day 15).

Figure 3:
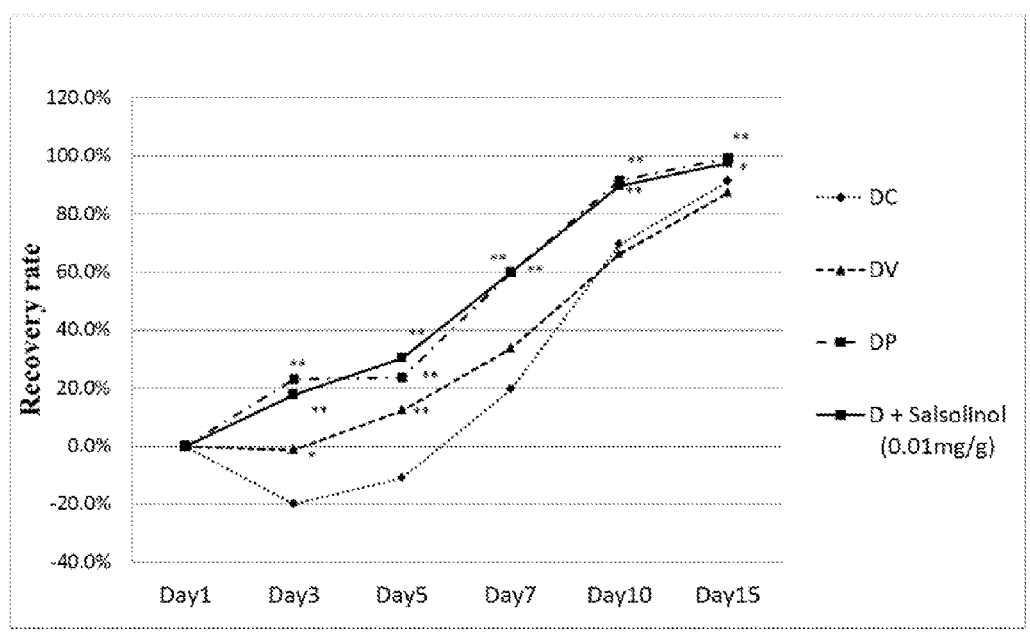
FIG. 3 shows the recovery rates of the wounds of STZ induced diabetic rats without treatment (DC), STZ induced diabetic rats treated with vehicle (DV), Swivazin® (DP, positive control), and salsolinol (D+Salsolinol, compound of the invention) for 14 days.

The groups of STZ induced diabetic rats treated with salsolinol (D+Salsolinol) were compared with the groups without treatment (DC) or the groups treated with vehicle (DV), and Swivazin® (DP, positive control). As shown in FIG. 3, the wounds of the DP and D+Salsolinol groups were recovered quickly in the beginning and having the recovery rates over 97% at Day 15. The group treated with salsolinol (D+Salsolinol) showed significantly increased recovery rate, and there is no obvious difference between the group treated with salsolinol (D+Salsolinol) and Swivazin® (DP).

In summary, salsolinol, one example of the present invention, provides significantly improved efficacy in diabetic wound healing, and has potential for developing a medicament for diabetic wound healing.

We claim:

1. A method for diabetic wound healing in a subject comprising
applying to the diabetic wound in said subject a pharmaceutical composition comprising a pharmaceutically acceptable carrier and a therapeutically effective amount of a compound having the general Formula I:

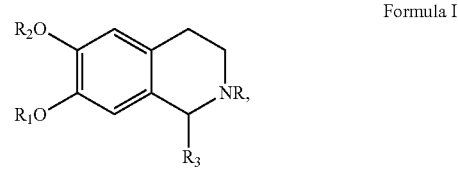

Formula I wherein R, $R_1$ and $R_2$ are each independently H, alkyl or acyl ($R_a$CO) group; $R_3$ is H, alkyl or substituted benzyl group; wherein $R_a$ is H or alkyl group.

2. The method of claim 1, wherein said substituted benzyl group has the following Formula II:

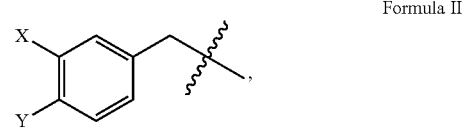

Formula II wherein X and Y are each independently H, OH, methoxy (OMe) or acyloxy ($R_b$CO—O—) group;
wherein $R_b$ is H or alkyl group.

3. The method of claim 1, wherein the compound is salsolinol.

* * * * *